United States Patent
Levine et al.

(10) Patent No.: US 7,324,844 B1
(45) Date of Patent: Jan. 29, 2008

(54) IMPLANTABLE CARDIAC STIMULATION SYSTEM AND METHOD FOR MEASURING ATRIOVENTRICULAR CONDUCTION AND ADJUSTING ATRIOVENTRICULAR HYSTERESIS

(75) Inventors: Paul A. Levine, Santa Clarita, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 404 days.

(21) Appl. No.: 10/879,444

(22) Filed: Jun. 28, 2004

Related U.S. Application Data

(63) Continuation of application No. 10/039,414, filed on Jan. 4, 2002, now Pat. No. 6,925,326, which is a continuation-in-part of application No. 09/952,902, filed on Sep. 12, 2001, now Pat. No. 6,792,307.

(51) Int. Cl.
*A61B 5/04* (2006.01)
*A61N 1/00* (2006.01)

(52) U.S. Cl. ......................... 600/510; 607/27

(58) Field of Classification Search ................. 600/510, 600/509; 607/9, 17, 7, 13, 15, 16, 27
See application file for complete search history.

(56) References Cited

U.S. PATENT DOCUMENTS

| | | | |
|---|---|---|---|
| 4,263,915 A | 4/1981 | McDonald et al. | ... 128/419 PG |
| 4,856,523 A | 8/1989 | Sholder et al. | ....... 128/419 PG |
| 5,318,594 A | 6/1994 | Limousin et al. | .............. 607/9 |
| 5,340,361 A | 8/1994 | Sholder | ...................... 607/24 |
| 5,417,714 A | 5/1995 | Levine et al. | .................. 607/9 |
| 5,690,689 A | 11/1997 | Sholder | ...................... 607/24 |
| 5,713,930 A * | 2/1998 | van der Veen et al. | ....... 607/25 |
| 5,741,308 A | 4/1998 | Sholder | ........................ 607/9 |
| 5,814,077 A | 9/1998 | Sholder et al. | ................ 607/9 |
| 6,081,747 A | 6/2000 | Levine et al. | .................. 607/9 |
| 6,312,388 B1 * | 11/2001 | Marcovecchio et al. | .... 600/508 |

FOREIGN PATENT DOCUMENTS

| EP | 0 494 487 A2 | 7/1991 |
|---|---|---|
| EP | 0 597 728 B1 | 11/1993 |

* cited by examiner

*Primary Examiner*—Mark Bockelman

(57) ABSTRACT

An implantable cardiac stimulation device and method measure atrioventricular conduction times and automatically adjust an atrioventricular delay time based on the measured conduction time values.

9 Claims, 9 Drawing Sheets

IMPLANTABLE CARDIAC STIMULATION SYSTEM AND METHOD FOR MEASURING ATRIOVENTRICULAR CONDUCTION AND ADJUSTING ATRIOVENTRICULAR HYSTERESIS

CROSS-REFERENCE TO RELATED APPLICATIONS

This application is a continuation of U.S. patent application Ser. No. 10/039,414, filed Jan. 4, 2002, which is a continuation-in-part of copending U.S. patent application Ser. No. 09/952,902, filed Sep. 12, 2001.

TECHNICAL FIELD

The devices and methods described herein relate generally to programmable cardiac stimulating devices. More specifically, an implantable stimulation device and associated method are disclosed for automatically monitoring atrioventricular conduction time and for providing automatic adjustment of an AV hysteresis interval.

BACKGROUND

Dual-chamber pacemakers and implantable cardioverter defibrillators require manual programming of numerous programmable parameters including but not limited to: choice of pacing mode, atrioventricular delay, atrioventricular hysteresis (AV hysteresis), and other parameters such as atrial sensitivity, ventricular sensitivity, post-ventricular atrial refractory period, post-ventricular atrial blanking period, ventricular refractory period, ventricular output, atrial output, upper rate limit, base rate, sleep rate, sensor slope, sensor threshold, and so forth. The programming of these parameters can be inaccurate and time consuming, and requires skilled medical expertise to accomplish.

For example, the choice of the pacing mode is a therapeutic decision made by the medical practitioner at the time of device implant. However, the optimal pacing mode may and does change over time as the patient's clinical condition or disease state changes. For example, a patient requiring dual chamber stimulation may in fact have intermittent atrioventricular conduction. At times when atrioventricular conduction is intact, single chamber atrial stimulation, or AAI mode, has been found to be therapeutically superior to dual chamber stimulation. Generally, such a patient would be paced in a dual chamber mode, for example DDD mode, but when an intrinsic R-wave is detected, ventricular stimulation is inhibited to allow natural heart conduction to occur. Stimulation devices capable of such functional mode switching are readily available.

A problem arises, however, in that the atrioventricular interval, which is the interval that must expire without R-wave detection following an atrial stimulation pulse before a ventricular stimulation pulse is delivered, is typically programmed to a very short value during dual chamber stimulation. A relatively short atrioventricular interval, also referred to as the AV interval has been found to give hemodynamic benefit during dual chamber stimulation in some special circumstances like hypertrophic cardiomyopathy, and when AV block is present but may be deleterious in the setting of normal conduction and a normal ventricular activation sequence. A short AV interval, however, is likely to be shorter than the natural atrial-ventricular conduction time (referred to as AV conduction time) of the heart. A short AV interval will preclude the detection of the intrinsic R-waves when AV conduction is intact because ventricular stimulation will occur before natural AV conduction has had time to occur. This situation may be deleterious in the setting of normal AV conduction and a normal ventricular activation sequence. The stimulation device usurps control over the natural conduction of the heart.

One disadvantage of this pacemaker competition with natural heart conduction is that natural AV conduction, when intact, has been found to be more beneficial to the patient than dual-chamber stimulation. Another disadvantage is that predominate ventricular stimulation in a patient with intact AV conduction unnecessarily wastes pacemaker battery life.

These problems have been addressed by adding positive hysteresis to the AV interval. AV hysteresis is an additional time period added to the AV interval during ventricular sensing. In essence, the interval that must expire before a ventricular stimulation pulse is delivered is extended by the AV hysteresis, allowing more time to sense for naturally conducted R-waves. Once ventricular stimulation is initiated, the ventricular stimulation pulses are then delivered at the programmed AV interval for a variable duration based on time or number of cycles.

The AV hysteresis is typically a programmable value that can be enabled or disabled. If enabled, it is commonly programmed to a setting between approximately 10 and 120 msec. Programming of the AV hysteresis, however, has been confusing to medical practitioners in that, first, the resulting stimulation rate is different than the sensing rate. Second, to determine an appropriate AV hysteresis, the AV interval must be temporarily programmed to a very long interval, then the AR interval (defined as the time interval between an atrial stimulation pulse and the subsequently sensed R-wave) must be measured. The minimum AV hysteresis is preferably the difference between the programmed AV interval and the measured AR interval. Since this measurement can be a time-consuming task, in practice, an arbitrary setting is often chosen. An arbitrary setting, however, may cause problems in that an insufficiently long hysteresis interval may result in fusion beats. Too short of an AV hysteresis setting would be ineffective because it does not allow a greater degree of R-wave detection.

Furthermore, a problem still exists, in that once ventricular stimulation is initiated at the programmed AV interval, it will continue to predominate over the natural heart rhythm. Attempts in overcoming this problem generally include temporarily extending the programmed AV interval by the AV hysteresis interval periodically during ventricular stimulation to allow for detection of an intrinsic R-wave in case AV conduction has returned. Reference is made to U.S. Pat. No. 5,814,077 to Sholder et al., U.S. Pat. No. 5,417,714 to Levine et al., and U.S. Pat. No. 5,318,594 to Limousin et al.

While these methods allow for periodic detection of restored AV conduction, the effect of temporal changes in the AV conduction time has not been fully addressed. Conventionally, the AV hysteresis is set to a fixed value that is either added to the AV interval as an additional time-out interval or not. The initial programmed value for the AV hysteresis may become inappropriate if changes in the AV conduction time occur. The AV conduction time may vary over time as a result of changes associated with the disease state of the patient, response to alterations in medical therapy, and even natural fluctuations occurring over a 24-hour period.

Thus automatically measuring the AV conduction time and monitoring variations in the AV conduction time over time would be desirable. Furthermore, automatic adjustment of the AV hysteresis based on the measured AV conduction time would be desirable to prevent pacemaker competition with natural heart conduction and thereby preserve battery life, as well as improve the performance of functional mode-switching stimulation devices in providing optimal dual-chamber stimulation therapy. As used herein, "functional mode-switching" refers, for example, to a DDD mode that behaves like one of the other modalities such as AAI, when conduction is present.

Since the AV conduction time can be different following an atrial stimulation pulse than following an intrinsic P-wave, determination of the AV conduction time following both events would be desirable so that a unique positive hysteresis interval could be determined and applied during atrial sensing (following atrial P-waves) as well as during atrial stimulation. In addition, storing the AV conduction time measurements over time so that they are available for future display would provide a valuable a diagnostic tool for the clinician in monitoring the progression of conduction disease or responses to medical therapy.

SUMMARY

What is provided is an implantable cardiac stimulation device and method for periodically measuring atrioventricular conduction times and automatically adjusting AV and PV hysteresis intervals. In accordance with one illustrative embodiment, AV conduction times are measured following either a stimulated or sensed atrial event by increasing the AV interval AVI (atrial-ventricular interval during atrial stimulation) or the PV interval (atrial-ventricular interval PVI following intrinsic atrial event) by a predetermined or programmable amount (also referred to as delta) and by sensing for an intrinsic R-wave. The various AV conduction times are stored for subsequent processing.

In one embodiment, statistical information is determined from the AV conduction time values, which is then used to set the AVI and PVI values, for example by adjusting respective hysteresis values.

In another embodiment, the acquired conduction time data is compared with stored data to monitor progression or regression of disease in the heart.

In yet another embodiment, the statistical information is generated and then stored for future use.

BRIEF DESCRIPTION OF THE DRAWINGS

The various features of the device and the manner of attaining them will be described in greater detail with reference to the following description, claims, and drawings, wherein reference numerals are reused, where appropriate, to indicate a correspondence between the referenced items, and wherein:

DETAILED DESCRIPTION

The following description is of a best mode presently contemplated for the device and method. This description is not to be taken in a limiting sense but is made merely for the purpose of describing the general principles of the device. In the description that follows, like numerals or reference designators will be used to refer to like parts or elements throughout.

A general cardiac stimulation device will be described in conjunction with FIGS. 1 and 2 in which the features included in the device described herein could be implemented. It is recognized, however, that numerous variations of such a device exist in which the methods described herein could be implemented.

Figure 1:
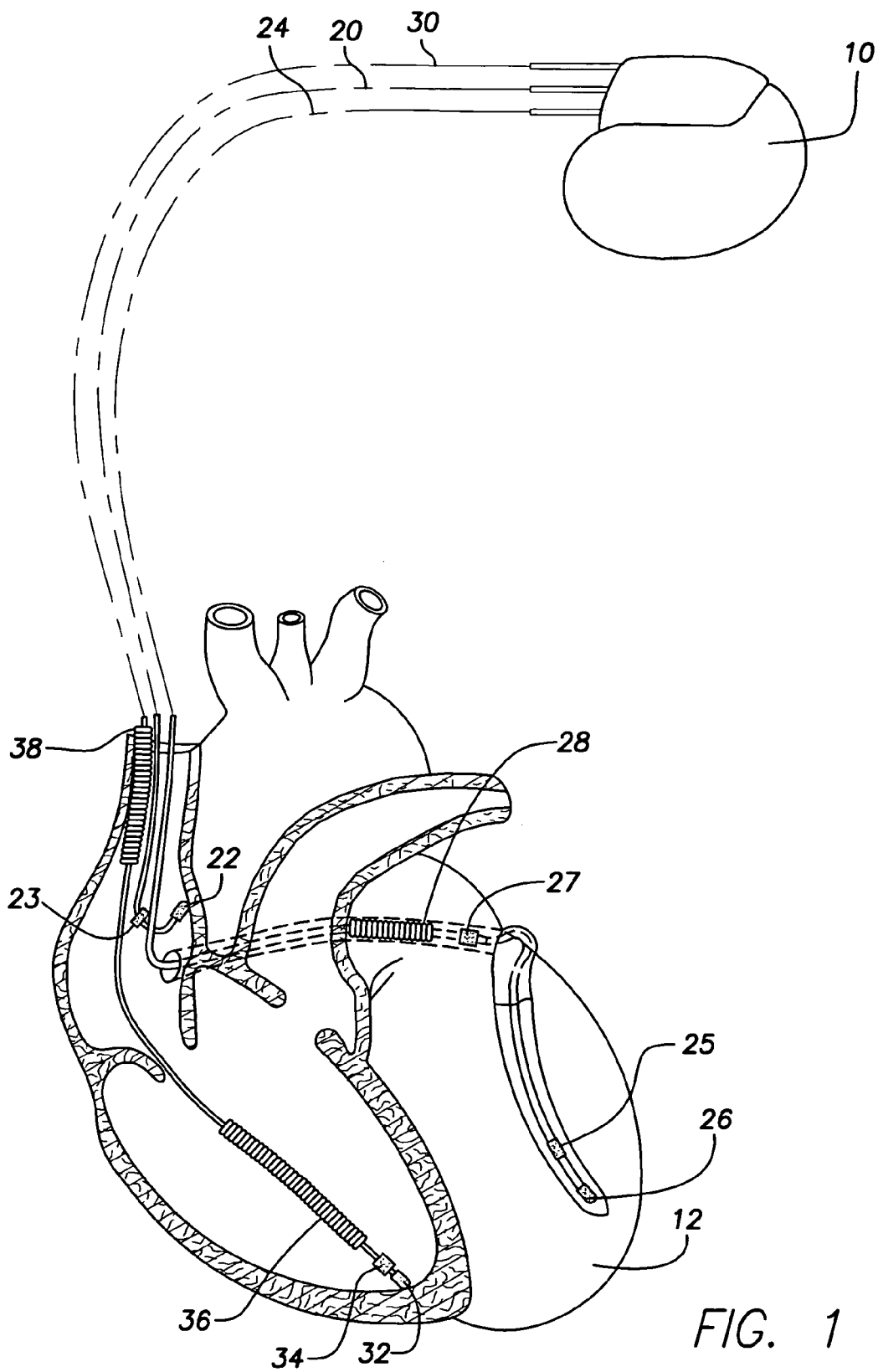
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using: at least a left ventricular tip electrode 26 for unipolar configurations or in combination with left ventricular ring electrode 25 for bipolar configurations; left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
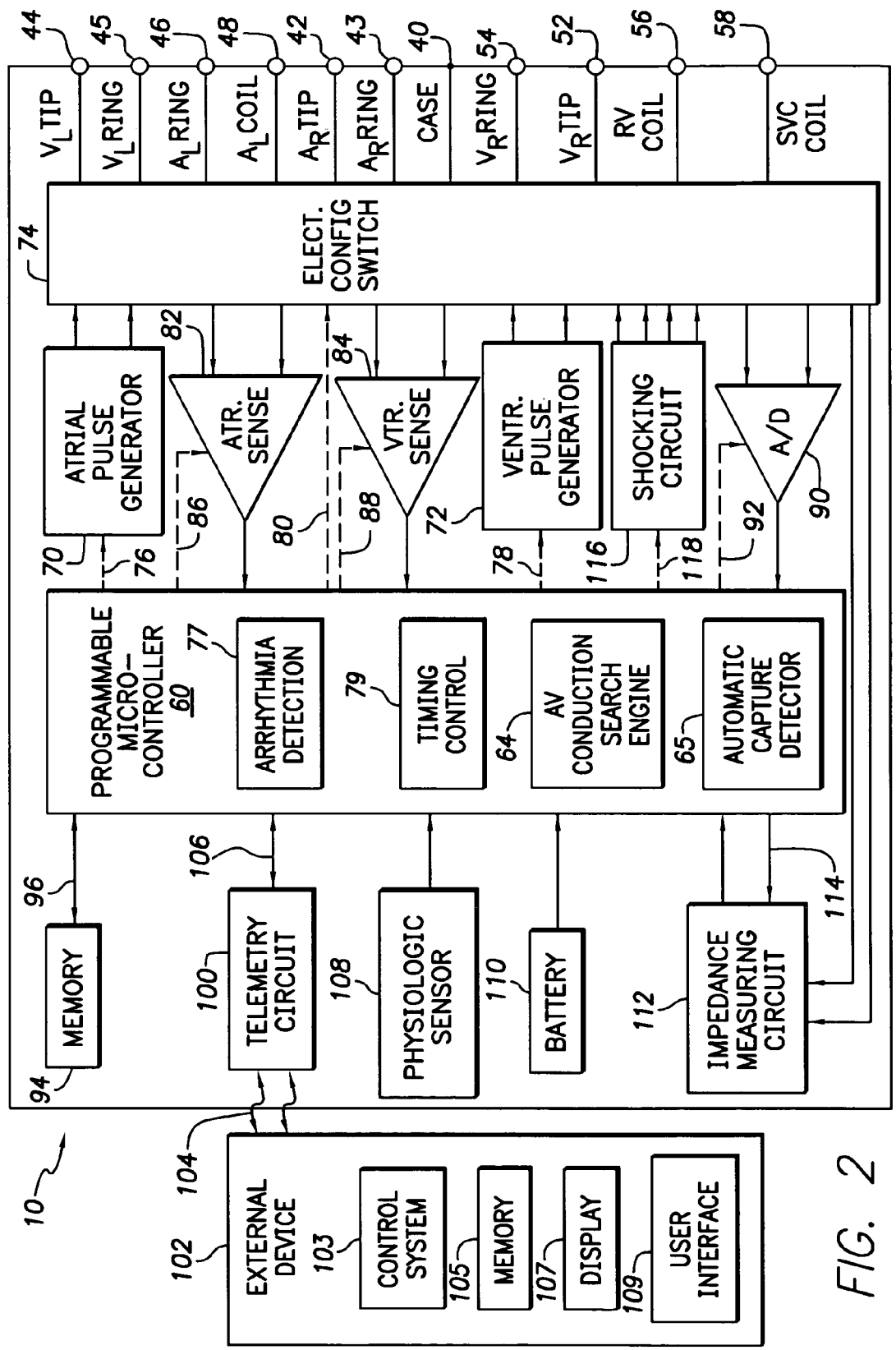
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 further includes a connector having a plurality of terminals, 42, 43, 44, 45, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal (AR TIP) 42 adapted for connection to the right atrial tip electrode 22. The connector may also include a right atrial ring terminal (AR RING) 43 for connection to the right atrial ring electrode 23.

To achieve left chamber sensing, pacing, and shocking, the connector includes at least a left ventricular tip terminal (VL TIP) 44, a left ventricular ring terminal (VL RING) 45, a left atrial ring terminal (AL RING) 46, and a left atrial shocking coil terminal (AL coil) 48, which are adapted for connection to the left ventricular tip electrode 26, the left ventricular ring electrode 25, the left atrial ring electrode 27, and the left atrial coil electrode 28, respectively.

To support right ventricular sensing, pacing and/or shocking, the connector further includes a right ventricular tip terminal (VR TIP) 52, a right ventricular ring terminal (VR RING) 54, a right ventricular shocking coil terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the device described herein. Rather, any suitable microcontroller 60 may be used that carries out the functions described herein. The use of microprocessor-based control circuits for performing timing and data analysis functions are known in the art.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrioventricular (AV) interval, atrial interconduction (A-A) delay, or ventricular interconduction (V-V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches as is known in the art. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate ventricular tachycardia (VT), high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. In the embodiment of FIG. 2, microcontroller 60 includes an automatic capture detector 65 that searches for an evoked response signal following a stimulation pulse during a detection window set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

Capture detection may occur, for example, on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

A feature of the stimulation device 10 is the ability to sense and store a relatively large amount of data (e.g., from the data acquisition system 90), which data may then be used for subsequent analysis to guide the programming of the stimulation device 10.

In accordance with the device described herein, an AV conduction search engine 64 included in microcontroller 60 executes algorithmic steps for measuring the AV conduction time, and the results are stored in the memory 94. These results will be subsequently used by the microcontroller 60 for appropriately adjusting the specific operating parameters of AV hysteresis and PV hysteresis as will be fully described herein.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

External device 102 is shown, in this embodiment, to include a control system 103 for controlling the programming and testing operations of the external device 102; a memory 105 for storing operational parameters or cardiac data downloaded from stimulation device 10; a display 107 for displaying cardiac data or results of issued programming commands; and a user interface 109 for entering programming commands or requests to retrieve data stored in stimulation device 10. In accordance with the device described herein, the telemetry circuit 100 will be used to download stored data associated with the measurement of AV conduction time such that it can be displayed on display 107 of external device 102.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV interval, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 µA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further shown in FIG. 2, the stimulation device 10 is shown as having an impedance measuring circuit 112 which is enabled by the microcontroller 60 by a control signal 114.

If it is a function of the stimulation device 10 to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
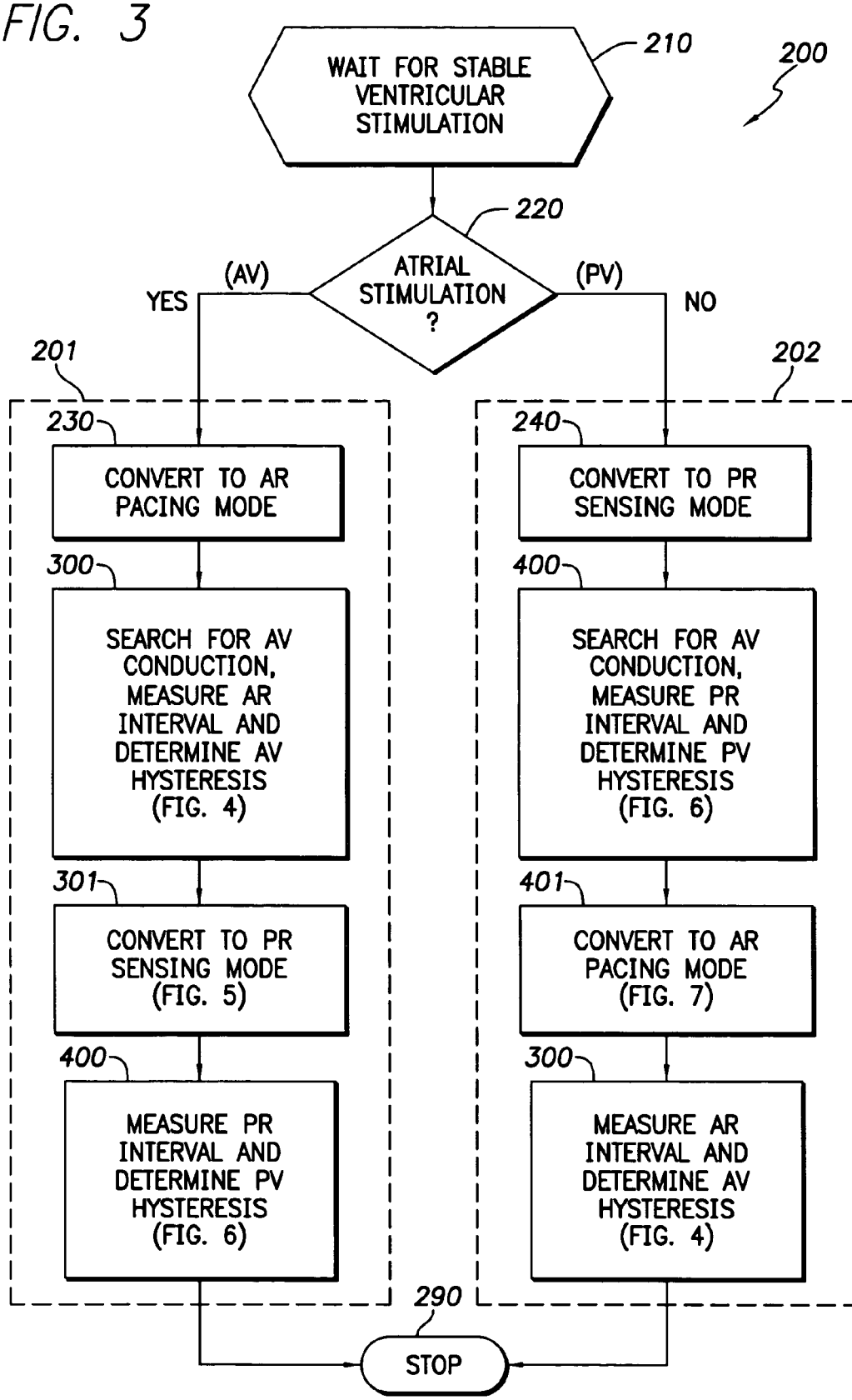
FIG. 3 is a flow chart providing an overview of the operations included in one embodiment of the device for measuring AV conduction time during atrial stimulation and during atrial sensing and automatically adjusting the corresponding AV and PV hysteresis intervals in the device of FIG. 2.

In FIG. 3, a flow chart is shown describing an overview of the operation and novel features implemented in one embodiment of the stimulation device 10. In this flow chart and other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device. Those skilled in the art may readily write such a control program based on the flow charts and other descriptions presented herein.

In this embodiment, the control program is comprised of multiple integrated program modules, with each module bearing responsibility for controlling one or more functions of the stimulation device 10. For example, one program module may control the delivery of stimulating pulses to the heart 12, while another may control the verification of ventricular capture and ventricular stimulation energy determination. In effect, each program module is a control program dedicated to a specific function or set of functions of the stimulation device 10.

In particular, a program module is implemented by the stimulation device 10 to periodically measure AV conduction time and automatically adjust AV and PV hysteresis intervals. At the time of implantation of the stimulation device 10 or during a follow-up office visit, stimulation mode, base stimulation rate, and the AV and PV intervals (also referred to as delays), among other parameters, are programmed into memory 94 by a medical practitioner using the external programmer 102 communicating with telemetry circuit 100. In addition, an algorithm 200 is enabled for measuring the AV conduction time and automatically adjusting the AV hysteresis and PV hysteresis. The methods included in the algorithm 200 are summarized in the flow chart of FIG. 3.

Once enabled, the algorithm (also referred to as method) 200 is executed by AV conduction search engine 64 starting at step 210 by verifying that the current operating mode of the device 10 is one of ventricular stimulation at a stable rate below a defined upper rate limit, for example not greater than 20 bpm above the programmed base rate. This upper rate limit is preferably programmable and is set to a level that reasonably prevents the algorithm 200 from executing or interrupting device 10 performance during high or unstable heart rates that might be arrhythmogenic or life-threatening in nature.

If rate stability is not immediately verified or the current ventricular stimulation rate is greater than the upper rate limit, the algorithm 200 is not executed. Rather, microprocessor 60 continues to monitor the rate and rhythm for a given period of time, preferably programmable, for example 48 hours. If rate stability criteria are not met within this time period, the algorithm 200 is aborted and will not be performed until it is re-enabled.

If stable ventricular stimulation below the upper rate limit is verified at step 210, the algorithm 200 continues by determining at decision step 220 the current stimulation mode of device 10. Depending on the current intrinsic heart rhythm, the stimulation device 10 could be in one of four pacing modes: 1) stimulating in the atrium and ventricle (AV rhythm or AV pacing), 2) sensing in the atrium and stimulating in the ventricle (PV rhythm or PV pacing), 3) stimulating in the atrium and sensing in the ventricle (PV rhythm or PV pacing), or 4) sensing in the atrium and the ventricle (PR rhythm or PR sensing). Since the algorithm 200 is intended to be applied in patients with intact but potentially and intermittently compromised AV conduction, an exemplary preferred stimulation mode is DDD stimulation. The algorithm 200 will be applied during ventricular stimulation modes, that is AV or PV rhythms.

Therefore at step 220, microprocessor 60 determines if the stimulation mode is one of atrial stimulation (AV rhythm) or atrial sensing (AR rhythm). If the stimulation device 10 is stimulating in the atrium, the method 200 proceeds to the operation sequence 201. If the stimulation device 10 is sensing in the atrium, the method 200 proceeds to the operation sequence 202.

Given that device 10 is stimulating in the atrium at decision step 220, the operation sequence 201 starts at step 230 by converting the stimulation mode of device 10 to an AR rhythm by extending the AV interval to allow time for intact atrioventricular conduction to occur. A sensed intrinsic ventricular depolarization will inhibit ventricular stimulation output from device 10. Operation sequence 201 then calls upon a method 300 (FIG. 4) to measure AV conduction time following stimulated atrial events. As it will be fully described later in conjunction with FIG. 4, the method 300 measures and stores the AV conduction time during atrial stimulation as the shortest AV interval at which sustained R-wave sensing occurs. Thus, the AV conduction time during atrial stimulation is referred to as the "AR interval." Using this measured AR interval, the method 300 calculates a positive hysteresis setting, AV hysteresis, by which to extend the programmed AV interval during ventricular stimulation in order to determine if AV conduction has returned.

Figure 5:
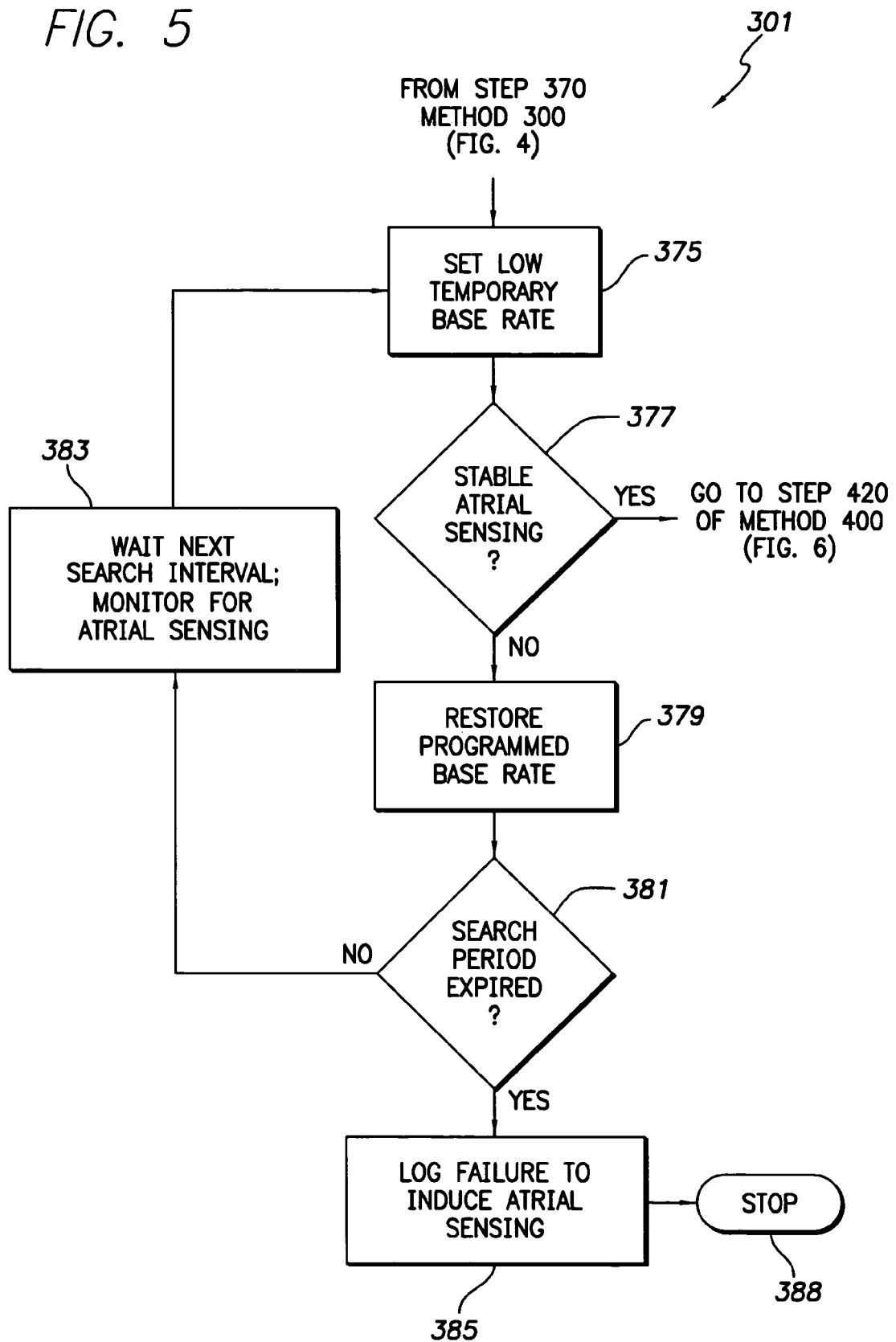
FIG. 5 is a flow chart depicting the method used by the algorithm of FIG. 3 for converting from atrial stimulation to atrial sensing.

Next a method 301, which will be described in detail in conjunction with FIG. 5, adjusts the stimulation device 10 settings so that atrial stimulation is inhibited and the device 10 begins sensing in the atrium. This conversion from atrial stimulation to atrial sensing allows the operation sequence 201 to call upon a method 400 to search for AV conduction following detected intrinsic P-waves.

Figure 6:
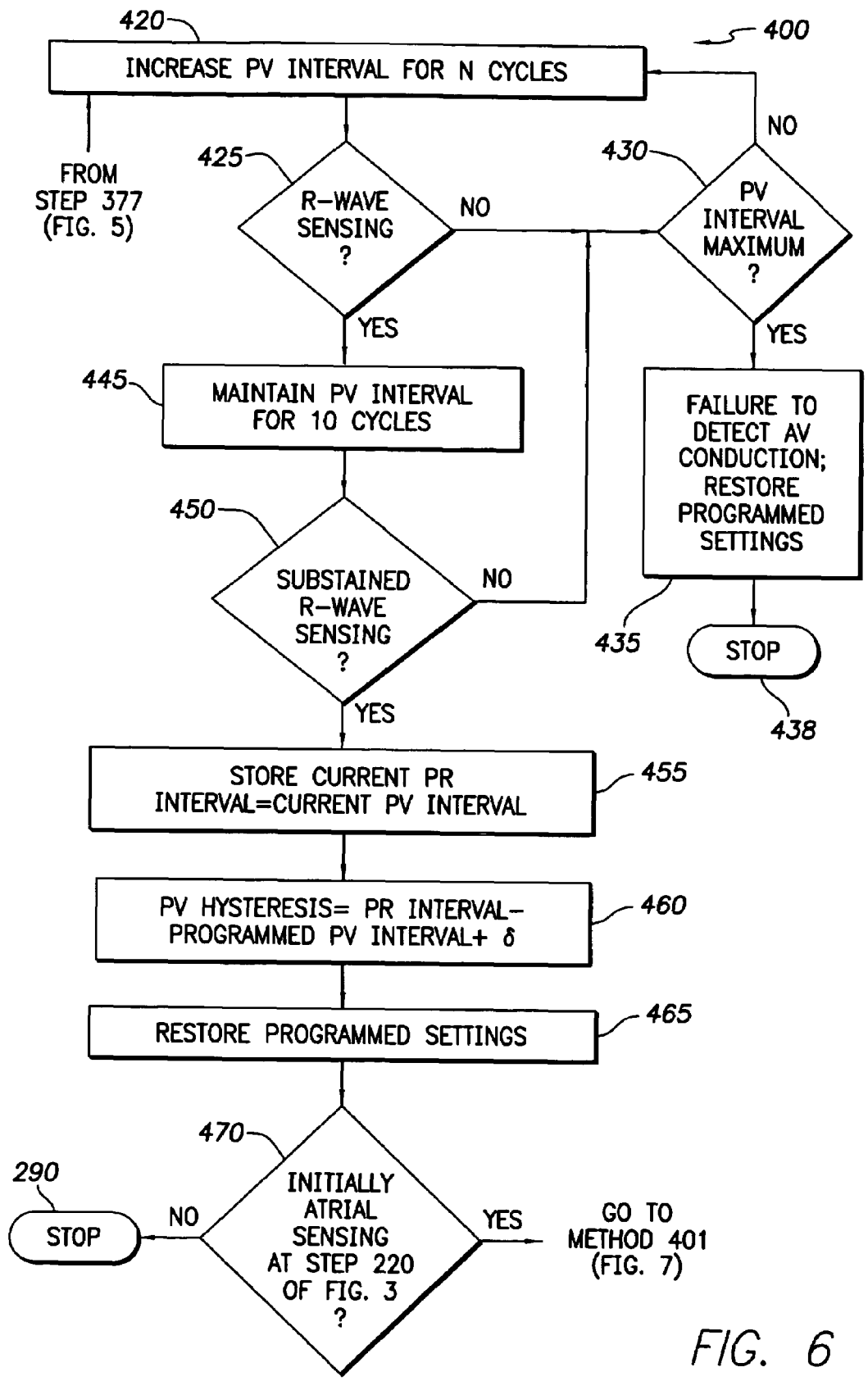
FIG. 6 is a flow chart depicting the method used by the algorithm of FIG. 3 for measuring the AV conduction time during atrial sensing and automatically adjusting a positive PV hysteresis interval.

As it will be described in conjunction with FIG. 6, method 400 measures and stores the AV conduction time during atrial sensing as the shortest PV interval at which sustained R-wave sensing occurs. Thus, the AV conduction time during atrial sensing is referred to as the "PR interval." Using this measured PR interval, the method 400 calculates a positive hysteresis setting, PV hysteresis, by which to extend the programmed PV interval during ventricular stimulation in order to determine if AV conduction has returned.

If the stimulation device 10 is sensing in the atrium rather than stimulating at decision step 220 in FIG. 3, the algorithm 200 proceeds to the operation sequence 202 starts at step 240 by converting the stimulation mode of device 10 to a PR rhythm by extending the PV interval to allow time for intact atrioventricular conduction to occur. A sensed intrinsic ventricular depolarization will inhibit ventricular stimulation output from device 10. Operation sequence 202 then and calls upon the method 400 (FIG. 6) to first measure the PR interval and calculate the PV hysteresis. Then, the method 401, to be described in detail in conjunction with FIG. 7, adjusts the device (10) settings to induce atrial stimulation, allowing operation sequence 202 to call upon method 300 (FIG. 4) to measure the AR interval and calculate the AV hysteresis.

Having measured and adjusted, or attempted to measure and adjust, the AR interval, PR interval, the AV hysteresis, and the PV hysteresis, the algorithm 200 is complete and is terminated at step 290.

Figure 4:
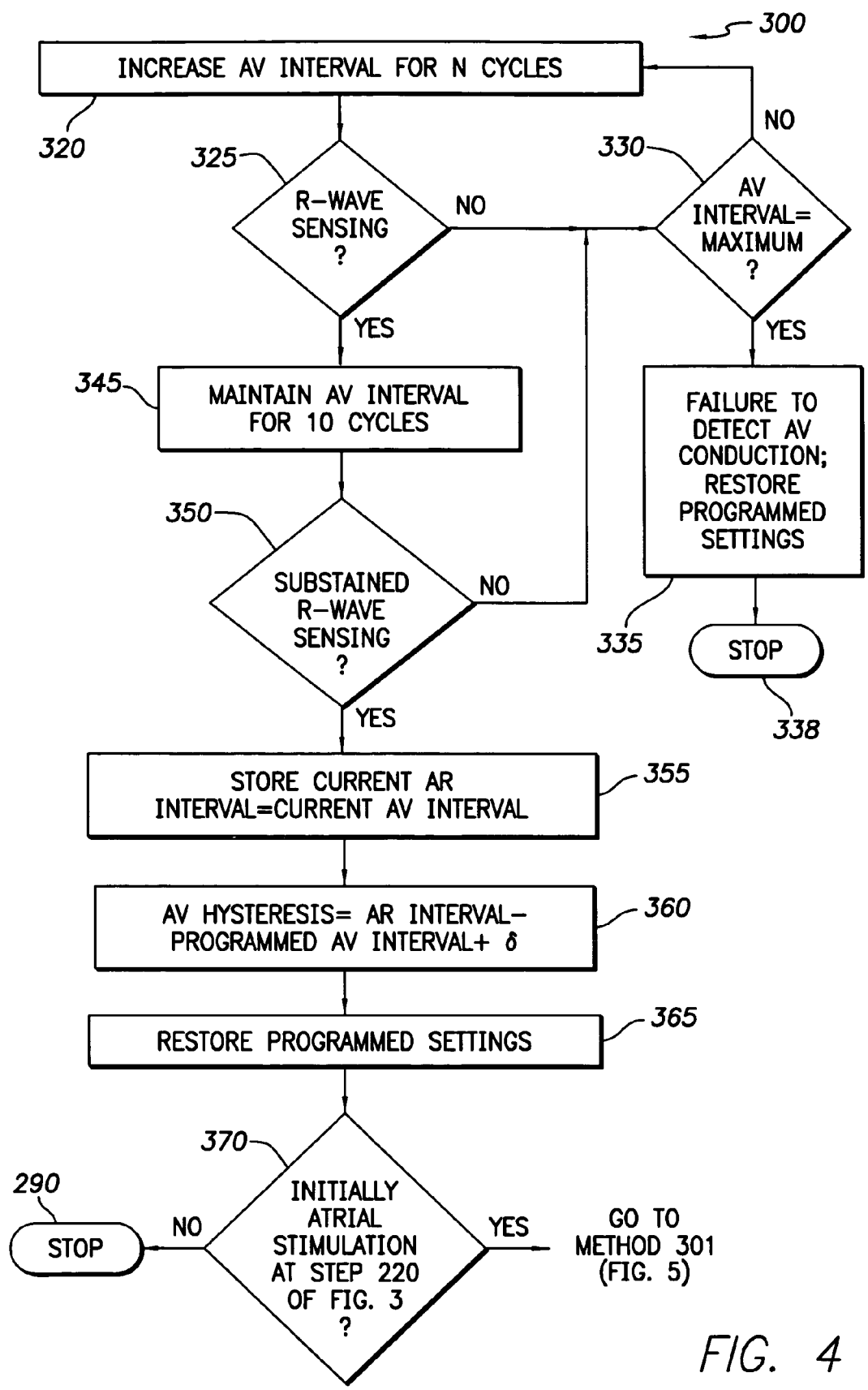
FIG. 4 is a flow chart depicting the method used by the algorithm of FIG. 3 for measuring the AV conduction time following during atrial stimulation and automatically and adjusting a positive AV hysteresis interval.

The method 300 for measuring the AV conduction time during atrial stimulation will now be described in detail with reference to FIG. 4. At step 320, the programmed AV interval setting is increased by a predefined interval, for example 10 msec, for a predefined number of cycles, 'n', preferably 3 cycles. The interval by which AV interval is increased may be a fixed or is, preferably, a programmable value. This value is typically equal to the minimum timing interval allowed by the stimulation device 10 timing control 79 or some multiple thereof. The smaller the increment, however, the more precise the AV conduction time measurement will be. The number of cycles for which the increased AV interval is maintained may also be fixed or, preferably, programmable, ranging from 1 to 10 cycles, preferably 3 cycles, for detecting a naturally-conducted R-wave following an atrial stimulation.

By increasing the AV interval, the interval following an atrial stimulation pulse delivered by atrial pulse generator 70 is effectively lengthened allowing ventricular sensing circuit 84 more time to detect a conducted R-wave that would follow the atrial stimulation pulse if AV conduction is intact. If an R-wave is not detected prior to the expiration of the increased AV interval, the ventricular pulse generator 78 will deliver a ventricular stimulation pulse at the end of the time-out interval consistent with the normal operation of the stimulation device 10.

Hence, at decision step 325, the microprocessor 60 determines if the ventricular sensing circuit 84 detects an R-wave during the 'n' cycles. If an R-wave is not detected, the increased AV interval setting is compared to a maximum allowable setting at decision step 330. The maximum allowable AV interval may be a fixed or programmable value stored in memory 94 and is preferably equal to the maximum available AV interval allowed by timing control 79, which is typically 300 to 350 msec. If the increased AV interval is less than the maximum allowed, then method 300 returns to step 320 to increase the AV interval a further step. This process repeats until an R-wave is detected at decision step 325 or until the increased AV interval reaches the maximum allowed. If the maximum AV interval is reached without R-wave sensing, a failure to detect a conducted R-wave is logged to memory 94 and the AV interval is restored to the original programmed value at step 335. No further attempt to measure the AV conduction time is made at this time, and algorithm 200 is terminated at step 338.

In one embodiment, repeated testing may occur at a later time, after a programmable number of cycles or time duration. Also, the total number of attempts that may be performed before the algorithm 200 (FIG. 3) is disabled. Once disabled, the algorithm 200 may be re-enabled via the external programmer 102 at the direction of the physician.

If an R-wave sensing does occur at decision step 325, then the increased AV interval setting is maintained for an additional number of cardiac cycles, preferably 10 cycles, at step 345, so that microprocessor 60 can determine if regular R-wave sensing is sustained at decision step 350. If R-wave sensing is not sustained, then AV conduction may be intermittent or slight fluctuations in the AV conduction time may be causing the present AV interval setting to be sometimes less than and sometimes greater than the AV conduction time. Thus, method 300 proceeds to decision step 330 to first verify that the increased AV interval is not equal to the maximum allowed, then continues to increase the AV interval (step 320) until sustained R-wave sensing is achieved.

If sustained R-wave sensing does occur as determined at decision step 350, then the increased AV interval setting is considered a measure of the AV conduction time during atrial stimulation. At step 355, the AR interval is set equal to the current value of the AV interval, which value is stored in memory 94 along with time and date information.

Next, microprocessor 60 calculates a new AV hysteresis setting at step 360 according to the following equation:

$$AV\ \text{hysteresis} = AR\ \text{interval} - \text{programmed}\ AV\ \text{interval} + \delta, \quad (1)$$

where "AR interval" is the measured AV conduction time following an atrial stimulation pulse as stored at step 355; programmed AV interval setting is the setting most recently programmed by the user; and δ is a predefined value, for example 30-50 msec, that acts as a safety margin to account for fluctuations in vagal tone.

Thus, the new AV hysteresis setting is equal to the difference between the measured AV conduction time during atrial stimulation and the programmed AV interval plus a small safety margin, δ.

If the additional safety margin δ causes the combined time-out interval of the AV interval plus the AV hysteresis to exceed the maximum AV interval allowed by timing control 79, then δ is decreased automatically such that this maximum AV interval is not exceeded. This adjustment and the new value of δ are logged to memory 94.

Having successfully measured the AR interval and adjusted the AV hysteresis, the programmed value for AV interval is restored at step 365. Thereafter, method 300 recalls at decision step 370 whether the stimulation device 10 was stimulating or sensing in the atrium at the initiation of the algorithm 200 (FIG. 3). If device 10 had been sensing in the atrium at the initiation of the algorithm 200, operation sequence 202 would have been initiated by calling upon method 400 first for the measuring the PR interval. Hence, the algorithm 200 would now be complete and thus terminated at step 290.

If the stimulation device 10 had been stimulating in the atrium at the initiation of the algorithm 200, then method 200 would have followed operation sequence 201 (FIG. 3) with method 300 being performed first as just described. The operation sequence 201 next calls upon method 301 for converting from atrial stimulation to atrial sensing to allow for PR interval measurement.

Method 301 will now be described in detail with reference to FIG. 5. Method 301 starts at step 375 by temporarily setting the base stimulation rate to a low rate, for example 30 pulses per minute. This low base rate is expected to inhibit atrial stimulation and allow the intrinsic heart rhythm to predominate so that the PR interval can be measured. Atrial sensing circuit 82 is expected to detect intrinsic P-waves at a rate less than the previously programmed base stimulation rate but greater than the temporary low base rate set at step 375, thus inhibiting the output of the atrial pulse generator 70.

If stable atrial sensing does not occur for a predefined number of cycles, for example 6 cycles, as determined at decision step 377, the programmed base stimulation rate is immediately restored at step 379 such that therapeutic stimulation needed by the patient is regained.

Microprocessor 60, however, will continue to monitor for stable atrial sensing (i.e., P-wave) throughout the course of a defined search period, for example 24 hours. To increase the likelihood of atrial sensing during the allowed search period, microprocessor 60 will periodically reset the low temporary base rate.

Thus, at decision step 381, microprocessor 60 determines if the allowed search period has expired, and if not, continues to monitor for stable atrial sensing while waiting a given search time interval, for example one hour, at step 383. When the search interval expires, or if an atrial sensing episode occurs, method 301 returns to step 375 to repeat an attempt to convert to stable atrial sensing by re-setting the low temporary base rate.

If stable atrial sensing never occurs during the allowed search period as determined at decision step 381, a failure to achieve stable atrial sensing is logged to memory 94 at step 385, and the algorithm 200 is terminated at step 388 with no further attempt to measure the PR interval or adjust the PV hysteresis at this time.

If stable atrial sensing is achieved at decision step 377 during the allowed search period, method 301 calls upon method 400 to measure the PR interval.

Method 400 will now be described in detail with reference to FIG. 6. Method 400 starts at step 420 by increasing the programmed PV interval by a predefined interval, for example 10 msec, for 'n' cycles, preferably 3 cycles. The interval by which the PV interval is lengthened and the number of cycles that the increased PV interval is maintained, are preferably programmable values and may be equal to or different than the values used by method 300 during measurement of the AR interval.

By increasing the PV interval, the interval following a P-wave sensed by atrial sensing circuit 82 is effectively lengthened allowing ventricular sensing circuit 84 more time to detect a conducted R-wave that would follow the intrinsic P-wave if AV conduction is intact. If a conducted R-wave is not detected prior to the expiration of the increased PV interval, ventricular pulse generator 78 will deliver a ventricular stimulation pulse at the end of the time-out interval consistent with the normal device 10 operation.

Hence, at decision step 425, the microprocessor 60 determines if ventricular sensing circuit 84 senses an R-wave during the increased PV interval. If no R-wave sensing occurs, the increased PV interval setting is compared to a maximum allowable PV interval setting at decision step 430. The maximum allowable setting may be a fixed or programmable value stored in memory 94 and is preferably equal to the maximum available PV interval allowed by timing control 79, which is typically 300 msec.

If the maximum allowable setting has not been reached at step 430, the PV interval continues to be increased at step 420 until R-wave sensing occurs at step 425. If the maximum PV interval is reached without R-wave sensing, failure to detect a conducted R-wave is logged to memory 94, and the programmed stimulation rate and PV interval settings are restored at step 435. No further attempt to measure the PR interval is made at this time and algorithm 200 is terminated at step 438.

If R-wave sensing does occur at decision step 425, the increased PV interval setting is maintained for a predefined number of cardiac cycles, preferably 10 cycles, at step 445, so that microprocessor 60 can determine if regular R-wave sensing is sustained at decision step 450. If R-wave sensing is not sustained, method 400 returns to decision step 430 to first verify that the increased PV interval is not equal to the maximum PV interval allowed. Method 400 then continues to increase the PV interval until sustained R-wave sensing is achieved at step 450.

If sustained R-wave sensing does occur as determined at decision step 450, then the increased PV interval setting is considered a measure of the AV conduction time during atrial sensing. At step 455, the PR interval is set equal to the increased PV interval and this value is stored in memory 94 along with time and date information.

Next, a new PV hysteresis setting is calculated at step 460 according to the following equation:

$$PV\text{ hysteresis} = PR\text{ interval} - \text{programmed } PV\text{ interval} + \delta, \quad (2)$$

where the PR interval is the measured AV conduction time following an intrinsic P-wave as stored at step 455; the programmed PV interval setting is the PV interval most recently programmed by the user; and $\delta$ is a predefined value, for example 30-50 msec, that acts as a safety margin to account for fluctuations in vagal tone.

Thus, the new PV hysteresis is equal to the difference between the measured AV conduction time during atrial sensing and the programmed PV interval plus a small safety margin, $\delta$.

If the additional $\delta$ causes the combined time-out interval of the PV interval plus the PV hysteresis to exceed the maximum PV interval allowed by timing control 79, then $\delta$ is decreased automatically such that this maximum PV interval is not exceeded. This adjustment and the new value of $\delta$ are logged to memory 94.

Having successfully measured the PR interval and adjusted the PV hysteresis setting, the programmed settings for base stimulation rate and PV interval are restored at step 465. Thereafter, method 400 recalls at decision step 470 whether the stimulation device 10 was sensing in the atrium (PV pacing state) at step 220 at the initiation of algorithm 200 (FIG. 3).

If the device 10 had been stimulating in the atrium at the initiation of algorithm 200 as determined at decision step 220, then method 200 would have followed the operation sequence 201 calling first upon method 300 for measuring the AR interval and adjusting the AV hysteresis and ending with method 400 for measuring the PR interval and adjusting the PV hysteresis exactly as just described. Hence, the algorithm 200 would be complete and therefore terminated at step 290.

If the stimulation device 10 had been sensing in the atrium (PV pacing state) at step 220, then the algorithm 200 would have followed the operation sequence 202, calling first upon method 400 to measure the PR interval and adjust the PV hysteresis, and will next call upon method 401 to convert from atrial sensing (PR sensing state) to atrial stimulation (AR pacing state) to allow for measurement of the AR interval and adjustment of the AV hysteresis.

Figure 7:
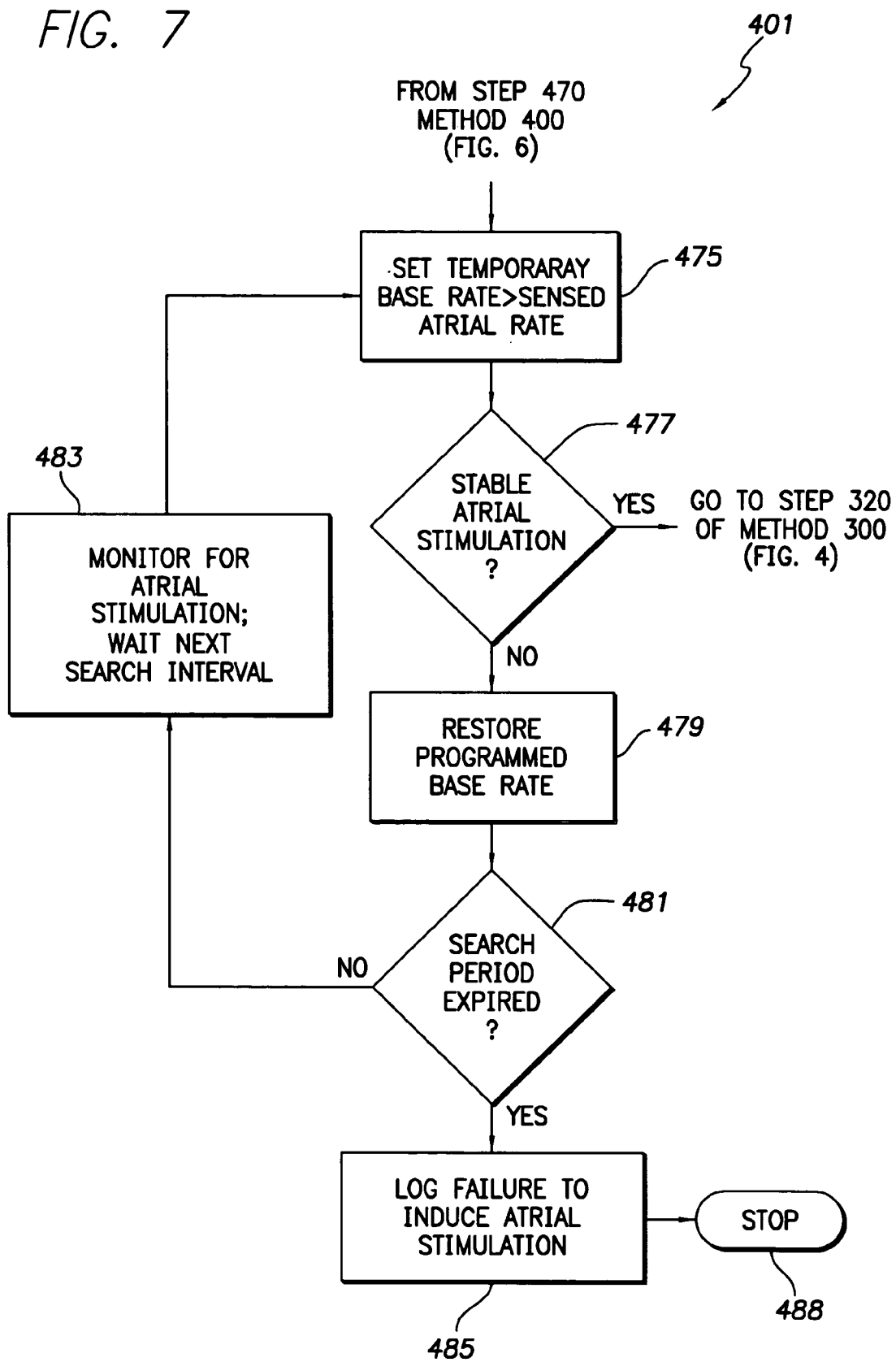
FIG. 7 is a flow chart depicting the method used by the algorithm of FIG. 3 for converting from atrial sensing to atrial stimulation.

Method 401 will now be described in detail with reference to FIG. 7. Method 401 begins at step 475 by setting a temporary base rate to a rate greater than the sensed atrial rate, for example 10 pulses per minute higher than the sensed rate. This high temporary base rate is expected to induce atrial stimulation to allow for measurement of the AV conduction time associated with atrial stimulation according to method 300. At decision step 477, microprocessor 60 determines if device 10 is in a stable atrial stimulation mode at the temporary high rate for a predefined number of cardiac cycles, for example 6 cycles.

If stable atrial stimulation is not detected immediately, the programmed base stimulation rate is restored at step 479. Microprocessor 60, however, will continue to monitor for stable atrial stimulation throughout the course of a defined search period, for example 24 hours. To increase the likelihood of atrial stimulation during the allowed search period, microprocessor 60 will also periodically re-set the high temporary base rate.

Therefore, at decision step 481, microprocessor 60 determines if the allowed search period has expired, and if not, continues to monitor for atrial stimulation while waiting a given search time interval, for example one hour, at step 483. When the search interval expires, or if an atrial stimulation episode occurs, method 401 returns to step 475 to repeat an attempt to convert to stable atrial stimulation by re-setting the temporary high base rate. If atrial stimulation never occurs during the allowed search period, a failure to induce atrial stimulation is logged to memory 94 at step 485, and the algorithm 200 is terminated at step 488 with no further attempt to determine the AR interval or adjust the AV hysteresis at this time.

If stable atrial stimulation does occur at step 477 during the allowed search period, method 401 calls upon method 300 to proceed with measuring the AR interval and calculates a new AV hysteresis as described previously in conjunction with FIG. 4.

Having determined, or attempted to determine, the AR interval, PR interval, AV hysteresis, and PV hysteresis, the algorithm 200 is now complete, and will not be executed again until it is re-enabled by a medical practitioner using the external programmer 102.

In an alternative embodiment, the algorithm 200 could be repeated at either fixed or programmable intervals of time, for example weekly, such that the AV hysteresis and the PV hysteresis are re-adjusted automatically if changes in the measured AR and PR intervals occur. Additionally, the results of such periodic monitoring, specifically the measured AR and PR intervals, are stored in memory 94 with coinciding time and date information. These data are made available later for graphic or tabular display on an external monitor 102 via telemetry circuit 100. A clinician can then readily observe changes in AV conduction over time. In this way, important diagnostic information may be revealed relating to AV conduction disease status or responses to medical therapy as well as indications for future stimulation device parameters.

Hence, in an alternative embodiment of the device, a programmable option is available for disabling automatic adjustment of the AV and PV hysteresis settings, so that the algorithm 200 functions as a diagnostic tool, collecting, storing, and displaying AV conduction time data over time. In this embodiment, the algorithm 200 is programmed to be repeated periodically according to individual patient need, for example hourly, daily or weekly, to collect the AV conduction time data (AR interval and PR interval), but no adjustment of hysteresis settings (AV hysteresis and PV hysteresis) is made. As a result, a useful diagnostic tool is provided for monitoring spontaneous fluctuations in the AV conduction time over a 24-hour period or for monitoring longer-term changes in the AV conduction time thereby tracking the progression of AV conduction disease.

In another embodiment, the AV and PV hysteresis intervals are calculated based on the variability of the AR or PR interval over time. In this embodiment, the determination of a positive hysteresis interval considers the probability of an R-wave occurring, rather than an actual occurrence, for a given AV or PV interval setting.

Figure 8:
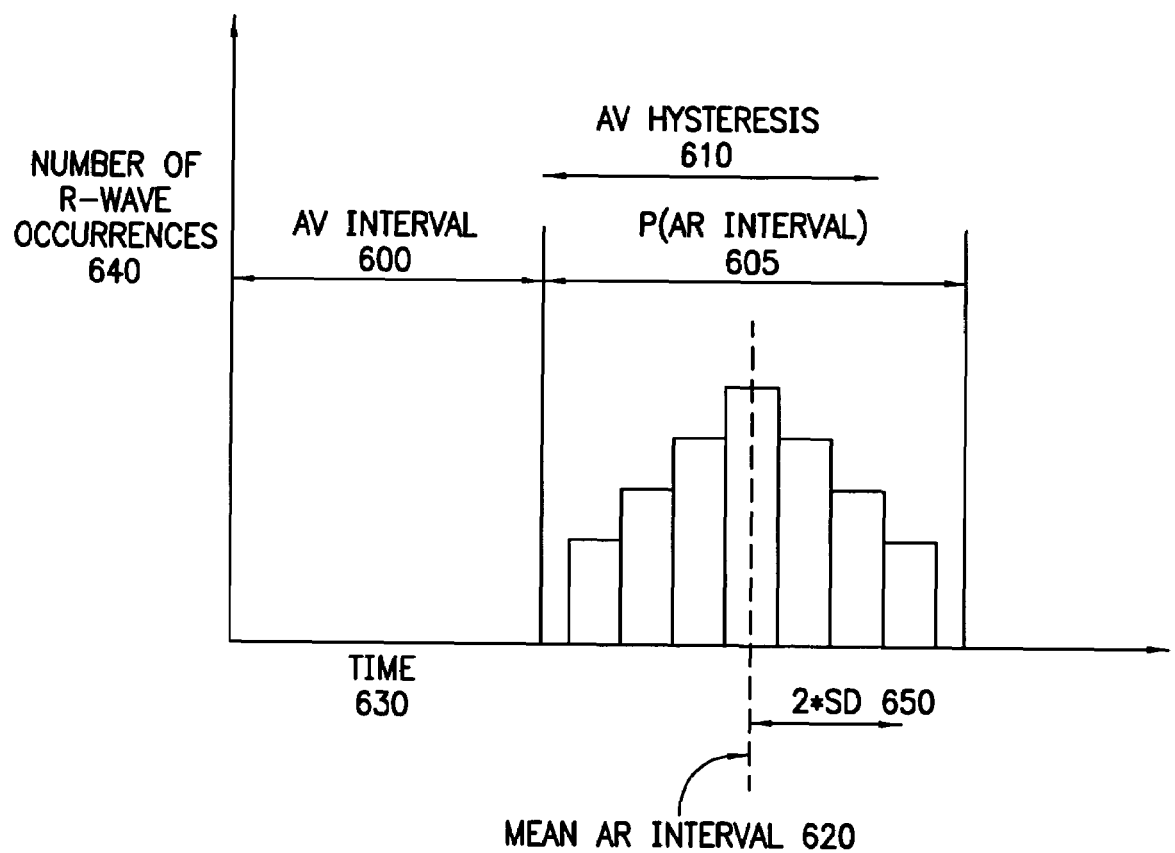
FIG. 8 is a graph illustrating the probability of an R-wave occurring following a given AV interval.

The graph shown in FIG. 8 illustrates the probability of R-waves occurring following a given AV interval 600. Time is represented by the x-axis 630, and the number of R-waves expected to occur is represented on the y-axis 640. Assuming an AV interval 600 is extended by a positive hysteresis by a given amount, the number of R-waves predicted to occur might follow a normal distribution as depicted in FIG. 8. The longer the time allowed for an R-wave to occur, the more R-waves will occur. However, the number of R-waves occurring at the longer intervals becomes fewer. Therefore to achieve a certain degree of confidence that a given percentage of R-waves will occur for a given positive hysteresis setting, the AV hysteresis 610 may be set based on the mean AR interval 620 and its standard deviation 650.

In order to calculate an AV or PV hysteresis based on the probability of R-waves occurring, the variation in the atrioventricular conduction time, measured as the AR or PR interval at which sustained R-wave sensing occurs, must be determined. Thus, a mean AR interval and a mean PR interval and standard deviations of these means are calculated from AR interval and PR interval results that have been stored in memory 94 over time.

The AV hysteresis can then be calculated as:

$$AV \text{ hysteresis} = (\text{mean } AR \text{ interval}) + \sigma * SD - AV \text{ interval} \quad (3)$$

where $\sigma$ is a constant, preferably equal to 2; SD is the standard deviation of the mean AR interval; and AV interval is the currently programmed AV interval.

Likewise, the PV hysteresis is calculated as:

$$PV \text{ hysteresis} = (\text{mean } PR \text{ interval}) + \sigma * SD - PV \text{ interval} \quad (4)$$

where $\sigma$ is a constant, preferably equal to 2; SD is the standard deviation of the mean PR interval; and PV interval is the currently programmed PV interval.

In these equations, the value of σ may be selected in order to achieve a desired degree of certainty that intrinsic R-waves will be detected. For example, a σ equal to 2 provides a 97.7 percent confidence interval that all R-waves will occur before expiration of the positive hysteresis setting. This a also serves to eliminate excessively long AR or PR intervals that may occur, which are most likely pathological.

Figure 9:
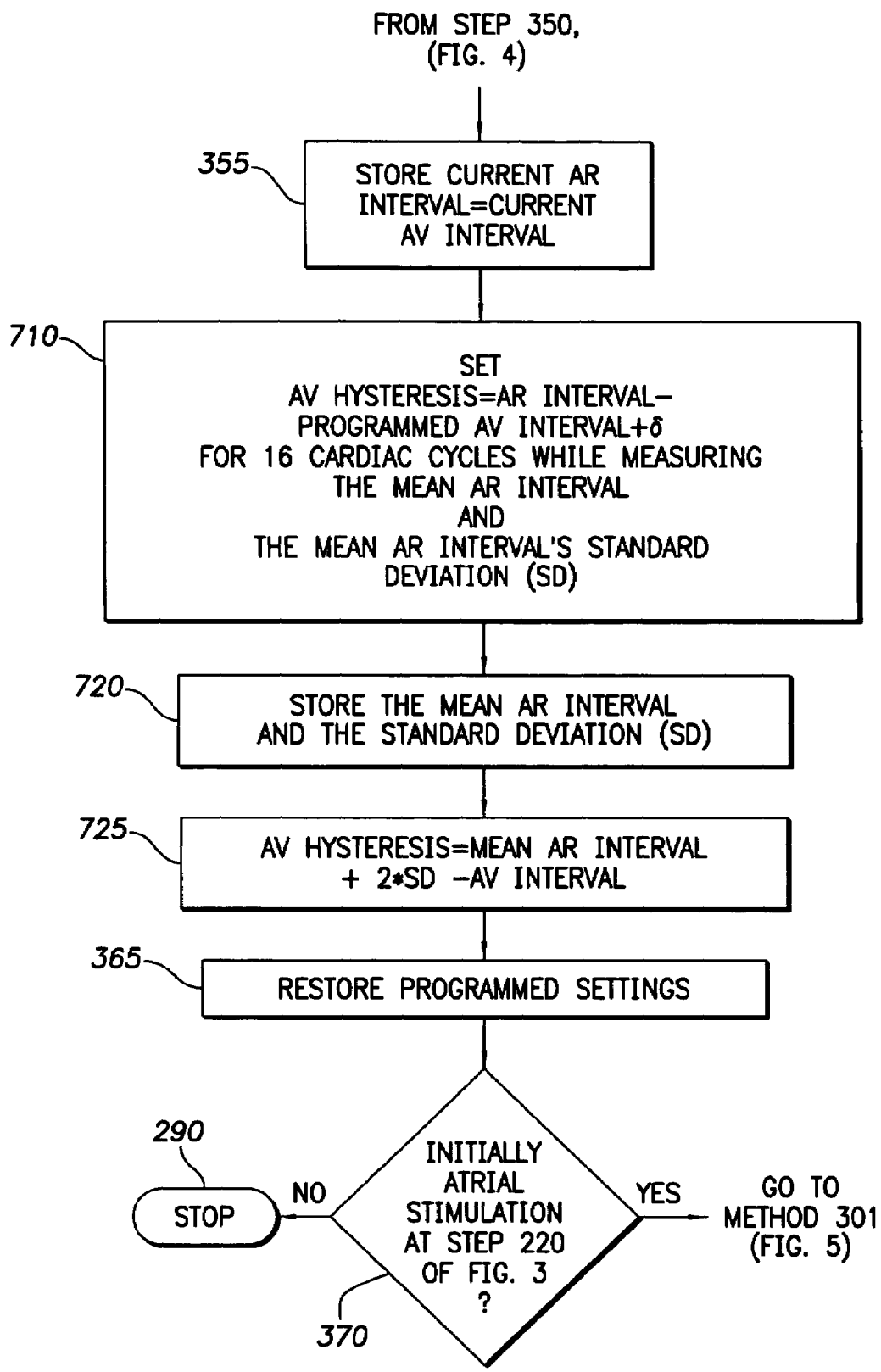
FIG. 9 is a flow chart illustrating an alternative method of calculating a positive AV hysteresis based on the variability of AV conduction time.

In this embodiment, the calculation of the AV hysteresis in method 300 (FIG. 4) is modified as shown in FIG. 9. An atrioventricular conduction search and measurement of the AR interval is performed using the same methods as described previously with reference to steps 320 through 350 of FIG. 4. The AR interval is set to the current AV interval and stored in memory 94 at step 355. At step 710 shown in FIG. 9, the AV hysteresis is set to the AR interval−Programmed AV interval+δ for a suitably statistically relevant number of cardiac cycles (e.g., 16). During this time the device will be primarily AR pacing and the mean AR interval is estimated along with the standard deviation (SD) of the AR interval, or other suitable statistical information is calculated. If AV pacing occurs during these statistical estimates of the AR interval, it may be ignored since it is an unlikely event and will not appreciably bias the estimate of the mean AR interval or the standard deviation (SD). At step 720, the mean of the AR intervals and the standard deviation of the mean are stored in memory 94, and are available for later review or processing. At step 725, the AV hysteresis is calculated according to equation 3 set forth above. The method 300 then continues as previously described by restoring the programmed AV interval setting at step 365 with the new AV hysteresis setting.

If the PV hysteresis setting has not yet been calculated, the method 300 continues to method 301. Similar modifications are made to the methods for calculating the PV hysteresis during method 400 wherein, after a new PR interval measurement is stored at step 455 (FIG. 6), a mean PR interval and its standard deviation are calculated from the stored PR interval values and used in equation 4 above for the calculation of the PV hysteresis setting.

In one embodiment, if the average AR interval (as computed from the recorded AR conduction time values) exceeds some preset threshold value, then the device is programmed to automatically set the AV delay to a default value (e.g., the programmed value), or to set the hysteresis to zero or a near-zero value to ensure that the AV delay is not excessively long.

Thus, a cardiac stimulating device has been described that automatically searches for AV conduction and, when AV conduction is found to be intact, measures the AV conduction time during both atrial stimulation and atrial sensing. Furthermore, the device provides automatic adjustment of unique positive AV and PV hysteresis settings for appropriately extending the programmed AV interval during atrial stimulation (AV pacing state) and the PV interval during atrial sensing (PV pacing state), respectively. This automatic hysteresis adjustment simplifies programming procedures required by the medical practitioner and functionally prevents pacemaker competition with the heart's natural conduction, thereby improving the stimulation device performance by ensuring that unnecessary ventricular stimulation does not occur when AV conduction is intact. Battery longevity is preserved and stimulation therapy is optimized since natural heart conduction pathways are allowed to control heart rhythm whenever possible. Furthermore, the device provides for the collection, storage and display of the AV conduction time measurements made over time as well as the variation in the AV conduction as measured by the standard deviation of the mean AV conduction (SD) measured over time, thus functioning as a diagnostic tool for monitoring conduction changes or disease or the effect of medications on the AV conduction. Similarly, the PV conduction properties may be collected, stored and displayed for diagnostic and therapeutic purposes. The descriptions provided herein are for the sake of illustration and are not intended to be exclusive.

What is claimed is:

1. A method of measuring atrioventricular conduction times in an implantable cardiac stimulation device, the method comprising:

periodically adjusting an atrioventricular delay until an intrinsic ventricular event is detected in response to a corresponding atrial event;

maintaining the adjusted atrioventricular delay for a predetermined period;

recording a plurality of conduction time values between atrial events and corresponding intrinsic ventricular events;

processing the conduction time values to determine a standard deviation of the conduction time values; and adjusting a hysteresis value as a function of the plurality of conduction time values and the standard deviation of the conduction time values.

2. The method of claim 1, wherein recording comprises recording a plurality of conduction times between intrinsic atrial events and corresponding intrinsic ventricular events.

3. The method of claim 1, wherein recording comprises recording a plurality of conduction times between stimulated atrial events and corresponding intrinsic ventricular events.

4. The method of claim 1, wherein processing further comprises calculating an average conduction time and a measure of variability of the conduction times.

5. The method of claim 1, further comprising setting an atrioventricular delay to a value based on the average conduction time and the measure of variability.

6. A method of measuring atrioventricular conduction times in an implantable cardiac stimulation device, the method comprising:

periodically adjusting an atrioventricular delay until an intrinsic ventricular event is detected in response to a corresponding atrial event;

maintaining the adjusted atrioventricular delay for a predetermined period;

recording a plurality of conduction time values between atrial events and corresponding intrinsic ventricular events during each of a plurality of predetermined periods;

processing the conduction time values to determine a standard deviation of the conduction times during each of the plurality of predetermined periods and adjusting a hysteresis value as a function of the plurality of conduction time values and the standard deviation of the conduction time values; and storing the standard deviation in memory for subsequent retrieval.

7. The method of claim 6, wherein recording comprises recording a plurality of conduction times between intrinsic atrial events and corresponding intrinsic ventricular events.

8. The method of claim 6, wherein recording comprises recording a plurality of conduction times between stimulated atrial events and corresponding intrinsic ventricular events.

9. The method of claim 6, wherein processing further comprises calculating an average conduction time and a measure of variability of the conduction times.

* * * * *